(12) United States Patent
Schütz et al.

(10) Patent No.: US 11,414,706 B2
(45) Date of Patent: Aug. 16, 2022

(54) METHOD OF DETERMINING A NUMERIC INDEX OF TUMOR-ASSOCIATED COPY NUMBER CHANGES OF CIRCULATING NUCLEIC ACIDS ASSOCIATED WITH PROSTATE CANCER

(71) Applicant: Chronix Biomedical, San Jose, CA (US)

(72) Inventors: Ekkehard Schütz, Göttingen (DE); Julia Beck, Gottingen (DE); Howard Urnovitz, San Jose, CA (US)

(73) Assignee: Chronix Biomedical, San Jose, CA (US)

( * ) Notice: Subject to any disclaimer, the term of this patent is extended or adjusted under 35 U.S.C. 154(b) by 777 days.

(21) Appl. No.: 15/985,649

(22) Filed: May 21, 2018

(65) Prior Publication Data

US 2018/0340233 A1    Nov. 29, 2018

Related U.S. Application Data

(63) Continuation of application No. 15/727,504, filed on Oct. 6, 2017, now abandoned, which is a continuation of application No. 14/799,989, filed on Jul. 15, 2015, now abandoned, which is a continuation of application No. 13/701,568, filed as application No. PCT/US2011/038780 on Jun. 1, 2011, now abandoned.

(60) Provisional application No. 61/351,708, filed on Jun. 4, 2010.

(51) Int. Cl.
*C12Q 1/6886* (2018.01)

(52) U.S. Cl.
CPC ..... *C12Q 1/6886* (2013.01); *C12Q 2600/158* (2013.01)

(58) Field of Classification Search
None
See application file for complete search history.

(56) References Cited

U.S. PATENT DOCUMENTS

| | | |
|---|---|---|
| 2008/0318243 A1 | 12/2008 | Haga |
| 2009/0162836 A1 | 6/2009 | Widschwendter |
| 2009/0280479 A1 | 11/2009 | Hoon et al. |

FOREIGN PATENT DOCUMENTS

| | | |
|---|---|---|
| WO | 2009/051842 A2 | 4/2009 |
| WO | 2010/053980 A2 | 5/2010 |

OTHER PUBLICATIONS

The International Search Report from PCT/US2011/038780, dated Aug. 13, 2012, 9 pages.
Allen et al. "Role of cell-free plasma DNA as a diagnostic marker for prostate cancer", *Ann. N.Y. Acad. Sci.* 1022(1): 76-80 (2004).
Bastian et al., "Prognostic value of preoperative serum cell-0free circulating DNA in men with prostate cancer undergoing radical prostatectomy", *Clinical Cancer Research* 13(18):5361-5367 (2007).
Ellinger et al.; "Noncancerous PTSG2 Dna fragments of apoptotic origin in sera of prostate cancer patients qualify as diagnostic and prognostic indicators"; *Int. J. Cancer*; 122:138-143 (Aug. 2007).
Felix et al., "Circulating tumour-associated plasma DNA represents an independent and informative predictor of prostate cancer", *BJU Intl.* 98(3): 544-548 (2006).
Müller et al.; "Comparison of genetic alterations detected in circulating microsatellite DNA in blood plasma samples of patients with prostate cancer and benign prostatic hyperplasia"; *Ann. N.Y. Acad. Sci.*; 1075:222-229 (2006).
Salani et al.; "Measurement of cyclin E genomic copy number and strand length in cell-free DNA distinguish malignant versus benign effusions"; *Clin. Cancer Res.*; 13(19):5805-5809 (Oct. 2007).
Sunami et al.; "Multimarker circulating DNA assay for assessing blood of prostate cancer patients"; *Clin. Chem.*; 55(3):559-567 (2009).
Umetani et al.; "Increased integrity of free circulating DNA in sera of patients with colorectal or periampullary cancer: direct quantitative PCR for ALU repeats"; *Clin. Chem.*; 52(6):1062-1069 (2006).
The Supplementary European Search Report, from EP Application No. 11790345, dated Oct. 15, 2013, 16 pages.
GenBankAccession No. AL356498 (version AL356498.10). "Human DNA Sequence from Clone RP11-341G2 on chromosome 9 contains a ubiquitin pseudogene and a DiGeorge syndrome-related protein pseudogene, complete sequence." Jan. 13, 2009, 28 pages.
GenBankAccession No. AL356285 (version AL356285.9). "Human DNA sequence from clone RP11-569O4 on chromosome 13 contains the 5' end of the XPO4 gene for likely ortholog of mouse exportin 4, a CCR4-NOT transcription complex, subunit 4 (CNOT4) (NOT4, NOT4H, CLONE243) pseudogene, a heterogenous nuclear ribonucleo protein A1 (HNRPA1)(HNRNPA1) pseudogene, a pseudogene similar to part of peptidoprolylisomerase A (cyclophilin A) (PPIA), a Laminin receptor 1 (67kD, ribosomal protein SA)(LAMR1)(LRP, p40, RPSA, 37LRP, LAMBR) pseudogene, the ' end ofthe LATS2 gene for LATS, large tumor suppressor, homolog 2 (LATS (large tumor suppressor, *Drosophila*) homolog2), two novel genesand 3 CpG islands, complete sequence." Jan. 13, 2009, 46 pages.

(Continued)

Primary Examiner — G Steven Vanni

(74) Attorney, Agent, or Firm — Kilpatrick Townsend & Stockton LLP

(57) ABSTRACT

The invention provides methods and reagents for diagnosing prostate cancer that are based on the detection of biomarkers in the circulating nucleic acids from a patient to be evaluated.

3 Claims, 1 Drawing Sheet
Specification includes a Sequence Listing.

(56) References Cited

OTHER PUBLICATIONS

Papadopoulou et al., "Cell-free DNA and RNA in plasma as a new molecular marker for prostate and breast cancer", *Ann. N.Y. Acad. Sci.* 10 75: (2006), 235-243.
Schwarzenbach et al., "Cell-free tumorDNA in blood plasmaasa marker for circulating tumor cells in prostate cancer", *Clin. Cancer Res.* 15(3): (2009) 1032-1038.

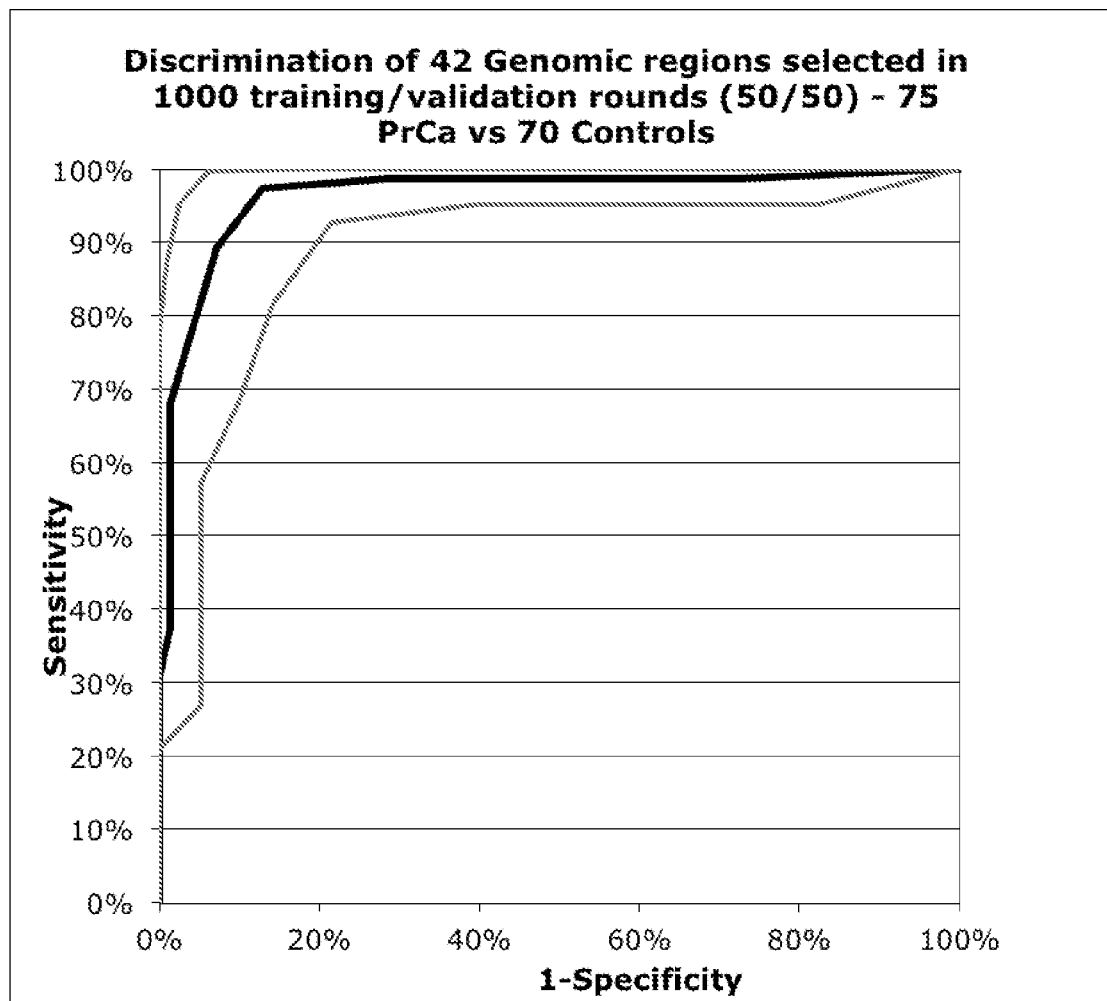

METHOD OF DETERMINING A NUMERIC INDEX OF TUMOR-ASSOCIATED COPY NUMBER CHANGES OF CIRCULATING NUCLEIC ACIDS ASSOCIATED WITH PROSTATE CANCER

CROSS-REFERENCE TO RELATED APPLICATIONS

This application is a continuation of U.S. application Ser. No. 15/727,504, filed Oct. 6, 2017, which is a continuation of U.S. application Ser. No. 14/799,989, filed Jul. 15, 2015, which claims priority to U.S. application Ser. No. 13/701,568, filed Feb. 19, 2013; which is a U.S. National Phase of PCT/US2011/038780, filed Jun. 1, 2011; which claims benefit of U.S. provisional application No. 61/351,708, filed Jun. 4, 2010. Each application is herein incorporated by reference.

REFERENCE TO SEQUENCE LISTING

This application includes a Sequence Listing as a text file named SEQ_083443-1090036-001340US.TXT created Jul. 30, 2018 and containing 1,480,314 bytes. The material contained in this text file is incorporated by reference in its entirety for all purposes.

BACKGROUND OF THE INVENTION

Methods to detect prostate cancer, including PSA tests, are extremely unreliable (see, e.g., Wever et al., *J Natl Cancer Inst* 2010;102:352-355, 2010; Schröder et al., *N. Engl. J. Med* 360:1320-1328, 2009). There is a need for effective detection methods. This invention addresses that need.

BRIEF SUMMARY OF THE INVENTION

The invention is based, in part, on the discovery of circulating nucleic acids (CNA) biomarkers associated with prostate cancer. In some embodiments, the CNA biomarkers are nucleic acid sequences, in the current invention DNA sequences, that are present in the blood, e.g., in a serum or plasma sample, of a prostate cancer patient, but are rarely present, if at all, in the blood, e.g., a serum or plasma sample, obtained from a normal individual, i.e., in the context of this invention, an individual that does not have prostate cancer. In some embodiments, the CNA biomarkers are nucleic acid sequences, in the current invention DNA sequences, i.e., DNA fragments, that are present in the blood, e.g., in a serum or plasma sample, of a normal individual, but are rarely present, if at all, in the blood, e.g., a serum or plasma sample, obtained from a prostate cancer patient.

Accordingly, in one aspect, the invention provides a method of analyzing CNA in a sample (blood, serum or plasma) from a patient comprising detecting the presence of at least one cell-free DNA having a nucleotide sequence falling within a chromosomal region set forth in Tables 2-5 (or having a nucleotide sequence that is part of one of the sequences set forth in Tables A-D) in the sample. In some embodiments, detecting the presence of, or the amount of, the at least one biomarker comprises detecting a cell-free DNA molecule having between 50 and 400 consecutive nucleotides of a unique sequence within a chromosomal region as set forth in Tables 2-5 (or of a unique sequence set forth in Tables A-D).

In one embodiment, a method of analyzing circulating free DNA in a patient sample is provided, comprising determining, in a sample that is blood, serum or plasma, the presence or absence, or the amount of, at least 2, 3, 4, 5, 7, 8, 9, 10, 15, 20, 30, 40, or at least 50 cell-free DNA molecules each having a sequence falling within a different chromosomal region set forth in Table 2, 3, 4, or 5, and preferably the sequences of the cell-free DNA molecules are free of repetitive element. In preferred embodiments, the cell-free DNA molecules have sequences falling within different chromosomal regions in the same table selected from Tables 2-5.

In another aspect, the present invention provides a kit including two or more (e.g., at least 2, 3, 4, 5, 6, 7, 8, 9, 10, 12, 15, 20, 25, 30, 40, or at least 50, but less than 115) sets of oligonucleotides. Each set comprises one or more oligonucleotides with a nucleotide sequence falling within one single chromosomal region that is set forth in Tables 2-5. Preferably, different oligonucleotide sets correspond to different chromosomal regions within the same table selected from Tables 2-5. Also, preferably the oligonucleotides are free of repetitive element. Optionally, the oligonucleotides are attached to one or more solid substrates such as microchips and beads.

In another aspect, the present invention provides a method of diagnosing or screening for prostate cancer in a patient. The method includes the steps of: (a) determining, in a sample that is blood, serum or plasma from a patient, the presence or absence or the amount of, at least 2, 3, 4, 5, 7, 8, 9, 10, 15, 20, 30, 40, or at least 50 cell-free DNA molecules each having a sequence falling within a different chromosomal region set forth in Table 2, 3, or 4; and (b) correlating the presence of, or an increased amount of, said first and second cell-free DNAs with an increased likelihood that the patient has prostate cancer. Preferably, the sequences of the cell-free DNA molecules are free of repetitive element. In preferred embodiments, the cell-free DNA molecules have sequences falling within different chromosomal regions in the same table chosen from Tables 2-4.

In one aspect, the invention provides a method of identifying a patient that has a CNA biomarker associated with prostate cancer, the method comprising detecting the presence of at least one biomarker set forth in Table 2, Table 3, or Table 4 in a CNA sample obtained from serum or plasma from the patient. A biomarker can be identified using any number of methods, including sequencing of CNA as well as use of a probe or probe set to detect the presence of the biomarker.

In some embodiments, the invention provides a method of identifying a patient that has a CNA biomarker that is associated with the absence of prostate cancer, the method comprising detecting the presence of at least one biomarker set forth in Table 5 in a CNA sample from serum or plasma from the patient. A biomarker can be identified using any number of methods, including sequencing of CNA as well as use of a probe or probe set to detect the presence of the biomarker.

In a further aspect, the invention provides a kit for identifying a patient that has a biomarker for prostate cancer and/or that has a biomarker associated with a normal individual that does not have prostate cancer, wherein the kit comprises at least one polynucleotide probe to a biomarker set forth in Table 2, 3, 4, or 5. Preferably, such a kit comprises probes to multiple biomarkers, e.g., at least 2, 3, 4, 5, 10, 20, 30, 40, 50, or more, of the biomarkers set forth in Tables 2-5. In some embodiments, the kit also includes an electronic device or computer software to compare the hybridization patterns of the CNA in the patient sample to a prostate cancer data set comprising a listing of biomarkers that are present in prostate cancer patient CNA, but not CNA samples from normal individuals.

In some embodiments, the presence of the at least one biomarker in CNA is determined by sequencing. In some embodiments, the presence of the at least one biomarker in CNA is determined using an array. In some embodiments, the presence of the at least one biomarker in CNA is determined using an assay that comprises an amplification reaction, such as a polymerase chain reaction (PCR). In some embodiments, a nucleic acid array forming a probe set comprising probes to two or more chromosomal regions set forth in Tables 2-5 is employed. In some embodiments, a nucleic acid array forming a probe set comprising 2, 3, 4, 5, 6, 7, 8, 9, 10 or more chromosomal regions, or all of the chromosomal regions, set forth in Table 2 is employed. In some embodiments, a nucleic acid array forming a probe set comprising 2, 3, 4, 5, 6, 7, 8, 9, 10, or more chromosomal regions, or all of the chromosomal regions, set forth in Table 3 is employed. In some embodiments, a nucleic acid array forming a probe set comprising 2, 3, 4, 5, 6, 7, 8, 9, 10 or more chromosomal regions, or all of the chromosomal regions, set forth in Table 4 is employed. In some embodiments, a nucleic acid array forming a probe set comprising two or more chromosomal regions, or all of the chromosomal regions set forth in Table 5 is employed.

In an additional aspect, the invention provides a method of detecting prostate cancer in a patient that has, or is suspected of having, prostate cancer, the method comprising contacting DNA from the serum or plasma sample with a probe that selectively hybridizes to a sequence present on a chromosomal region described herein, e.g., a sequence set forth in Tables A-D under conditions in which the probe selectively hybridizes to the sequence; and detecting the presence or absence of hybridization of the probe, wherein the presence of hybridization to a sequence set forth in Table A, B, or C is indicative of prostate cancer.

The Tables of Sequences A, B, C, and D provide examples of sequences corresponding to the chromosome regions set forth in Table 2, Table 3, Table 4, and Table 5, respectively. The designation (N)x in Tables A-D refer to repetitive element sequences. Table A contains SEQ ID NOS:1-1072. Table B contains SEQ ID NOS:1073-1916. Table C contains SEQ ID NOS:1917-1968. Table D contains SEQ ID NOS: 1969-1972.

BRIEF DESCRIPTION OF THE DRAWINGS

FIG. 1 provides an example of a ROC curve using the 42 highest ranking regions of the chromosomal regions identified in Tables 4 and 5, collectively. The actual ROC curve-build from score sums is given together with the 95% confidence limits.

DETAILED DESCRIPTION OF THE INVENTION

As used herein, a "biomarker" as used herein refers to a nucleic acid sequence that corresponds to a chromosomal region, where the presence of the nucleic acid in CNA is associated with prostate cancer.

In the current invention, a "chromosomal region" listed in any one of Tables 1 to 5 refers to the region of the chromosome that corresponds to the nucleotide positions indicated in the tables. The nucleotide positions on the chromosomes are numbered according to *Homo sapiens* (human) genome, build 37.1 as of June 2010 (Tables 1-3) and *Homo sapiens* (human) genome, build 36 as of March 2006 (Table 4, 5). As understood in the art, there are naturally occurring polymorphisms in the genome of individuals. Thus, each chromosome region listed in the tables encompasses allelic variants as well as the particular sequence in the database, e.g., the sequences in Tables A-D corresponds to the chromosomal regions noted. An allelic variant typically has at least 95% identity, often at least 96%, at least 97%, at least 98%, or at least 99% identity to the sequence of a chromosomal region noted in the Tables that is present in a particular database, e.g., the National Center for Biotechnology Information (*Homo sapiens* Build 37.1 at the ncbi nlm nih mapview website.) Percent identity can be determined using well known algorithms, including the BLAST algorithm, e.g., set to the default parameters. Further, it is understood that the nucleotide sequences of the chromosomes may be improved upon as errors in the current database are discovered and corrected. The term "chromosomal region" encompasses any variant or corrected version of the same region as defined in Tables 1-5. Given the information provided in the tables in the present disclosure, especially in view of the sequences listed in Tables A-D, a skilled person in the art will be able to understand the chromosomal regions used for the present invention even after new variants are discovered or errors are corrected.

"Detecting the presence of a chromosomal region" in CNA in the context of this invention refers to detecting any sequence from a chromosomal region shown in Table 2, 3, 4, or 5, where the sequence detected can be assigned unambiguously to that chromosomal region. Thus, this term refers to the detection of unique sequences from the chromosomal regions. Methods of removing repetitive sequences from the analysis are known in the art and include use of blocking DNA, e.g., when the target nucleic acids are identified by hybridization. In some embodiments, typically where the presence of a prostate cancer biomarker is determined by sequencing the CNA from a patient, well known computer programs and manipulations can be used to remove repetitive sequences from the analysis (see, e.g., the EXAMPLES section). In addition, sequences that have multiple equally fitting alignment to the reference database are typically omitted from further analyses.

The term "detecting a biomarker" as used herein refers to detecting a sequence from a chromosomal region listed in Table 2, Table 3, Table 4, or Table 5. A biomarker is considered to be present if any nucleic acid sequence present in the CNA is unambiguously assigned to the chromosomal region.

The term "unambiguously assigned" in the context of this invention refers to determining that a DNA detected in the CNA of a patient is from a particular chromosomal region. Thus, in detection methods that employ hybridization, the probe hybridizes specifically to that region. In detection methods that employ amplification, the primer(s) hybridizes specifically to that region. In detection methods that employ sequencing, the sequence is assigned to that region based on well-known algorithms for identity, such as the BLAST algorithm using high stringent parameters, such as e<0.0001. In addition, such a sequence does not have a further equally fitting hit on the used database.

The term "circulating nucleic acids" refers to acellular nucleic acids that are present in the blood.

The term "circulating cell-free DNA" as used herein means free DNA molecules of 25 nucleotides or longer that are not contained within any intact cells in human blood, and can be obtained from human serum or plasma.

The term "hybridization" refers to the formation of a duplex structure by two single stranded nucleic acids due to complementary base pairing. Hybridization can occur between exactly complementary nucleic acid strands or between nucleic acid strands that contain minor regions of mismatch. As used herein, the term "substantially complementary" refers to sequences that are complementary except for minor regions of mismatch. Typically, the total number of mismatched nucleotides over a hybridizing region is not more than 3 nucleotides for sequences about 15 nucleotides in length. Conditions under which only exactly complementary nucleic acid strands will hybridize are referred to as "stringent" or "sequence-specific" hybridization conditions. Stable duplexes of substantially complementary nucleic acids can be achieved under less stringent hybridization conditions. Those skilled in the art of nucleic acid technology can determine duplex stability empirically considering a number of variables including, for example, the length and base pair concentration of the oligonucleotides, ionic strength, and incidence of mismatched base pairs. For example, computer software for calculating duplex stability is commercially available from National Biosciences, Inc. (Plymouth, Minn.); e.g., OLIGO version 5, or from DNA Software (Ann Arbor, Mich.), e.g., Visual OMP 6.

Stringent, sequence-specific hybridization conditions, under which an oligonucleotide will hybridize only to the target sequence, are well known in the art (see, e.g., the general references provided in the section on detecting polymorphisms in nucleic acid sequences). Stringent conditions are sequence-dependent and will be different in different circumstances. Generally, stringent conditions are selected to be about 5° C. lower to 5° C. higher than the thermal melting point (Tm) for the specific sequence at a defined ionic strength and pH. The Tm is the temperature (under defined ionic strength and pH) at which 50% of the duplex strands have dissociated. Relaxing the stringency of the hybridizing conditions will allow sequence mismatches to be tolerated; the degree of mismatch tolerated can be controlled by suitable adjustment of the hybridization conditions.

The term "primer" refers to an oligonucleotide that acts as a point of initiation of DNA synthesis under conditions in which synthesis of a primer extension product complementary to a nucleic acid strand is induced, i.e., in the presence of four different nucleoside triphosphates and an agent for polymerization (i.e., DNA polymerase or reverse transcriptase) in an appropriate buffer and at a suitable temperature. A primer is preferably a single-stranded oligodeoxyribonucleotide. The primer includes a "hybridizing region" exactly or substantially complementary to the target sequence, preferably about 15 to about 35 nucleotides in length. A primer oligonucleotide can either consist entirely of the hybridizing region or can contain additional features which allow for the detection, immobilization, or manipulation of the amplified product, but which do not alter the ability of the primer to serve as a starting reagent for DNA synthesis. For example, a nucleic acid sequence tail can be included at the 5' end of the primer that hybridizes to a capture oligonucleotide.

The term "probe" refers to an oligonucleotide that selectively hybridizes to a target nucleic acid under suitable conditions. A probe for detection of the biomarker sequences described herein can be any length, e.g., from 15-500 bp in length. Typically, in probe-based assays, hybridization probes that are less than 50 bp are preferred.

The term "target sequence" or "target region" refers to a region of a nucleic acid that is to be analyzed and comprises the sequence of interest.

As used herein, the terms "nucleic acid," "polynucleotide" and "oligonucleotide" refer to primers, probes, and oligomer fragments. The terms are not limited by length and are generic to linear polymers of polydeoxyribonucleotides (containing 2-deoxy-D-ribose), polyribonucleotides (containing D-ribose), and any other N-glycoside of a purine or pyrimidine base, or modified purine or pyrimidine bases. These terms include double- and single-stranded DNA, as well as double- and single-stranded RNA. Oligonucleotides for use in the invention may be used as primers and/or probes.

A nucleic acid, polynucleotide or oligonucleotide can comprise phosphodiester linkages or modified linkages including, but not limited to phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages.

A nucleic acid, polynucleotide or oligonucleotide can comprise the five biologically occurring bases (adenine, guanine, thymine, cytosine and uracil) and/or bases other than the five biologically occurring bases. These bases may serve a number of purposes, e.g., to stabilize or destabilize hybridization; to promote or inhibit probe degradation; or as attachment points for detectable moieties or quencher moieties. For example, a polynucleotide of the invention can contain one or more modified, non-standard, or derivatized base moieties, including, but not limited to, N6-methyladenine, N6-tert-butyl-benzyl-adenine, imidazole, substituted imidazoles, 5-fluorouracil, 5 bromouracil, 5-chlorouracil, 5-iodouracil, hypoxanthine, xanthine, 4-acetylcytosine, 5 (carboxyhydroxymethyl)uracil, 5 carboxymethylaminomethyl-2-thiouridine, 5 carboxymethylaminomethyluracil, dihydrouracil, beta-D-galactosylqueosine, inosine, N6 isopentenyladenine, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2 thiocytosine, 5-methyl-2-thiouracil, 2-thiouracil, 4-thiouracil, 5-methyluracil, uracil-5-oxyacetic acidmethylester, 3-(3-amino-3-N-2-carboxypropyl) uracil, (acp3)w, 2,6-diaminopurine, and 5-propynyl pyrimidine. Other examples of modified, non-standard, or derivatized base moieties may be found in U.S. Pat. Nos. 6,001,611; 5,955, 589; 5,844,106; 5,789,562; 5,750,343; 5,728,525; and 5,679,785, each of which is incorporated herein by reference in its entirety. Furthermore, a nucleic acid, polynucleotide or oligonucleotide can comprise one or more modified sugar moieties including, but not limited to, arabinose, 2-fluoroarabinose, xylulose, and a hexose.

The term "repetitive element" as used herein refers to a stretch of DNA sequence of at least 25 nucleotides in length that is present in the human genome in at least 50 copies.

The terms "arrays," "microarrays," and "DNA chips" are used herein interchangeably to refer to an array of distinct polynucleotides affixed to a substrate, such as glass, plastic, paper, nylon or other type of membrane, filter, chip, bead, or any other suitable solid support. The polynucleotides can be synthesized directly on the substrate, or synthesized separate from the substrate and then affixed to the substrate. The arrays are prepared using known methods.

Introduction

The invention is based, at least in part, on the identification CNA sequences from particular chromosomal regions that are present or at an increased amount in the blood of patients that have prostate cancer, but are rarely, if ever, present, or at a lower amount, in the blood of normal patients that do not have prostate cancer. The invention is also based, in part, on the identification of biomarkers in the CNA in normal individuals, i.e., in the context of this invention, individuals not diagnosed with prostate cancer, that are rarely, if ever, present in patients with prostate cancer. Thus, the invention provides methods and devices for analyzing for the presence of sequences from a chromosomal region corresponding to at least one of the chromosomal regions set forth in Table 2, Table, 3, Table 4, or Table 5.

Accordingly, in one aspect, the invention provides a method of analyzing CNA in a sample (blood, serum or plasma) from a patient comprising detecting the presence of, or an amount of, at least one circulating cell-free DNA having a nucleotide sequence of at least 25 nucleotides falling within a chromosomal region set forth in Table 2, 3, 4, o5 (or having a nucleotide sequence that is a part of one of the sequences set forth in Table A, B, C, or D). Preferably, the circulating cell-free DNA is free of repetitive element. In one embodiment, the patient is an individual suspected of or diagnosed with cancer, e.g., prostate cancer.

By "falling within" it is meant herein that the nucleotide sequence of a circulating cell-free DNA is substantially identical (e.g., greater than 95% identical) to a part of the nucleotide sequence of a chromosome region. In other words, the circulating cell-free DNA can hybridize to under stringent conditions, or be derived from, the chromosomal region.

In one embodiment, a method of analyzing circulating cell-free DNA in a patient sample is provided, comprising determining, in a sample that is blood, serum or plasma, the presence or the amount of, a plurality of circulating cell-free DNA molecules each having a sequence of at least 25 nucleotides in length falling within the same one single chromosomal region set forth in Table 2, Table 3, Table 4, or Table 5 (or each having a nucleotide sequence of at least 25 consecutive nucleotides in length that is a part of the same sequence set forth in Table A, Table B, Table C, or Table D). There may be two or more or any number of different circulating cell-free DNA molecules that are all derived from the same one chromosomal region set forth in Table 2, 3, 4, or 5, and in some embodiments, all such circulating cell-free DNA molecules are detected and/or the amounts thereof are determined.

Preferably the sequences of the circulating cell-free DNA molecules are free of repetitive elements.

In one embodiment, a method of analyzing circulating cell-free DNA in a patient sample is provided, comprising determining, in a sample that is blood, serum or plasma, the presence or absence or the amount of, at least 2, 3, 4, 5, 7, 8, 9, 10, 15, 20, 30, 40, or at least 50 circulating cell-free DNA molecules each having a sequence of at least 25 base pairs falling within a different chromosomal region set forth in Table 2, Table 3, Table 4, or Table 5 (or having a nucleotide sequence of at least 25, 40, 50, 60, 75 or 100 consecutive nucleotides in length that is a part of one of the sequences set forth in Table A, Table B, Table C, or Table D). Preferably the sequences of the circulating cell-free DNA molecules are free of repetitive elements. In preferred embodiments, the cell free DNA molecules have sequences falling within different chromosomal regions in the same table that is chosen from Tables 2-5. In one specific embodiment, the presence or absence or the amounts of, at least 2, 3, 4, 5, 7, 8, 9, 10, 15, 20, or at least 25, or of 30, 31, or 32, circulating cell-free DNA molecules are determined, the sequence of each falling within a different chromosomal region set forth in Table 2 (or having a nucleotide sequence of at least 25, 40, 50, 60, 75 or 100 consecutive nucleotides in length that is a part of one of the sequences set forth in Table A). In another specific embodiment, the presence or absence or the amounts of, at least 2, 3, 4, 5, 7, 8, 9, 10, or at least 15, or of 20, 21, or 22, circulating cell-free DNA molecules are determined, the sequence of each falling within a different chromosomal region set forth in Table 3 (or having a nucleotide sequence of at least 25, 40, 50, 60, 75 or 100 consecutive nucleotides in length that is a part of one of the sequences set forth in Table B). In one specific embodiment, the presence or absence or the amounts of, at least 2, 3, 4, 5, 7, 8, 9, 10, 15, 20, 25, 30, 35, 50, 45, or 50, or of 52, circulating cell-free DNA molecules are determined, the sequence of each falling within a different chromosomal region set forth in Table 4 (or having a nucleotide sequence of at least 25, 40, 50, 60, 75 or 100 consecutive nucleotides in length that is a part of one of the sequences set forth in Table C). In yet another specific embodiment, the presence or absence or the amounts of, at 1, 2, 3, or 4 circulating cell-free DNA molecules are determined each having a sequence falling within a different chromosomal region set forth in Table 5 (or having a nucleotide sequence of at least 25, 40, 50, 60, 75 or 100 consecutive nucleotides in length that is a part of one of the sequences set forth in Table D).

In a specific embodiment, the method of analyzing circulating cell-free DNA includes the steps of: isolating, from blood, serum or plasma sample of a patient, substantially all circulating cell-free DNA molecules having a length of at least 20, 25, 30, 40, 50, 75 or 100 consecutive nucleotides in length, or between 50 and 400 nucleotides in length, obtaining the sequence of each of the circulating cell-free DNA molecules, and comparing the sequence to one or more of the sequences set forth in Tables A-D to determine whether the sequence falls within a chromosomal region set forth in Table 2, 3, 4, or 5.

In another specific embodiment, the method of analyzing circulating cell-free DNA includes the steps of: isolating, from blood, serum or plasma sample of a patient, substantially all circulating cell-free DNA molecules having a length of at least 20, 25, 30, 40, 50, 75 or 100 consecutive nucleotides in length, or between 50 and 400 nucleotides in length, and contacting the circulating cell-free DNA molecules to a plurality of oligonucleotides (e.g., on a DNA chip or microarray) to determine if one of the circulating cell-free DNA molecules hybridizes to any one of the plurality of oligonucleotide probes under stringent conditions. Each of the oligonucleotide probes has a nucleotide sequence identical to a part of the sequence of a chromosomal region chosen from Tables 2-5 (or a sequence set forth in Tables A-D). Thus, if a circulating DNA molecule hybridizes under stringent conditions to one of the oligonucleotide probes, it indicates that the circulating DNA molecule has a nucleotide sequence falling within a chromosomal region set forth in Table 2, Table 3, Table 4, or Table 5.

In the above various embodiments, preferably the circulating cell-free DNA molecules have at least 25 consecutive nucleotides in length (preferably at least 50, 70, 80, 100, 120 or 200 consecutive nucleotides in length). More preferably, the circulating cell-free DNA molecules have between about 50 and about 300 or 400, preferably from about 75 and about 300 or 400, more preferably from about 100 to about 200 consecutive nucleotides of a unique sequence within a chromosomal region as set forth in Table 2, Table 3, Table 4, or Table 5 (or of a unique sequence set forth in Table A, Table B, Table C, or Table D).

In another aspect, the present invention provides a method of diagnosing or screening for prostate cancer in a patient. The method includes the steps of: (a) determining, in a sample that is blood, serum or plasma from a patient, the presence or absence or the amount of, at least 1, 2, 3, 4, 5, 7, 8, 9, 10, 15, 20, 30, 40, or at least 50 circulating cell-free DNA molecules each having a sequence of at least 25 nucleotides in length falling within a different chromosomal region set forth in Table 2, Table 3, or Table 4 (or having a nucleotide sequence of at least 25 consecutive nucleotides in length that is a part of one of the sequences set forth in Table A, Table B, or Table C); and (b) correlating the presence of or an increased amount of the circulating cell-free DNAs with an increased likelihood that the patient has prostate cancer.

Alternatively, the method of invention includes the steps of: (a) determining, in a sample that is blood, serum or plasma from a patient, the presence or absence or the amount of 1, 2, 3, or 4 circulating cell-free DNA molecules each having a sequence of at least 25 nucleotides in length falling within a different chromosomal region set forth in Table 5 (or having a nucleotide sequence of at least 25 consecutive nucleotides in length that is a part of one of the sequences set forth in Table D); and (b) correlating the presence of or an increased amount of the circulating cell-free DNAs with a decreased likelihood that the patient has prostate cancer.

When the steps of the above methods are applied to a patient diagnosed of cancer, the patient may be monitored for the status of prostate cancer, or for determining the treatment effect of a particular treatment regimen, or detecting cancer recurrence or relapse.

In the diagnosis/monitoring method of the present invention, preferably the sequences of the circulating cell-free DNA molecules are free of repetitive elements. In preferred embodiments, the cell free DNA molecules have sequences falling within different chromosomal regions in the same table chosen from Tables 2-5.

In one embodiment, a method of diagnosing prostate cancer in an individual is provided, comprising (a) determining the presence or absence or the amounts of, at least 2, 3, 4, 5, 7, 8, 9, 10, 15, 20, or at least 25, or of 30, 31, or 32, circulating cell-free DNA molecules the sequence of each falling within a different chromosomal region set forth in Table 2 (or having a nucleotide sequence of at least 25 consecutive nucleotides in length that is a part of one of the sequences set forth in Table A); and (b) correlating the presence of or an increased amount of, one or more of the circulating cell-free DNA molecules with an increased likelihood that the individual has prostate cancer or a recurrence of prostate cancer or a failure of treatment for prostate cancer.

In another embodiment, a method of diagnosing prostate cancer in an individual is provided, comprising (a) determining the presence or absence or the amounts of, at least 2, 3, 4, 5, 7, 8, 9, 10, or at least 15, or of 20, 21, or 22, circulating cell-free DNA molecules the sequence of each falling within a different chromosomal region set forth in Table 3 (or having a nucleotide sequence of at least 25 consecutive nucleotides in length that is a part of one of the sequences set forth in Table B); and (b) correlating the presence of, or an increased amount of, one or more of the circulating cell-free DNA molecules with an increased likelihood that the individual has prostate cancer or a recurrence of prostate cancer or a failure of treatment for prostate cancer.

In one embodiment, a method of diagnosing prostate cancer in an individual is provided, comprising (a) determining the presence or absence or the amounts of, at least 2, 3, 4, 5, 7, 8, 9, 10, 15, 20, 25, 30, 35, 40, 45, or 50, or of 52, circulating cell-free DNA molecules the sequence of each falling within a different chromosomal region set forth in Table 4 (or having a nucleotide sequence of at least 25 consecutive nucleotides in length that is a part of one of the sequences set forth in Table C); and (b) correlating the presence of or an increased amount of, one or more of the circulating cell-free DNA molecules with an increased likelihood that the individual has prostate cancer or a recurrence of prostate cancer or a failure of treatment for prostate cancer.

In one embodiment, a method of diagnosing/monitoring prostate cancer in an individual is provided, comprising (a) determining the presence or absence or the amounts of, 1, 2, 3, or 4 circulating cell-free DNA molecules the sequence of each falling within a different chromosomal region set forth in Table 5 (or having a nucleotide sequence of at least 25 consecutive nucleotides in length that is a part of one of the sequences set forth in Table D); and (b) correlating the presence of or an increased amount of, one or more of the circulating cell-free DNA molecules with an increased likelihood that the individual does not have prostatet cancer or a recurrence of prostate cancer or a failure of treatment for prostate cancer.

In yet another embodiment, the method of diagnosing, monitoring or screening for prostate cancer in a patient, includes determining, in a sample that is blood, serum or plasma from the patient, the presence or absence or the total amount of, each and all circulating cell-free DNAs each having a sequence falling within the same one single chromosomal region set forth in Table 2, Table 3, or Table 4; and correlating the presence of one of said circulating cell-free DNAs or an increased total amount of said circulating cell-free DNAs, with an increased likelihood that said patient has prostate cancer, or recurrence of prostate cancer. In other words, there can be any number of, and typically many, different circulating cell-free DNA molecules derived from one single same chromosomal region set forth in Table 2, Table 3, or Table 4, and all of such different circulating cell-free DNA molecules are detected and/or the amount each or all is determined, and correlation with the status of prostate cancer is made.

In a specific embodiment, substantially all circulating cell-free DNA molecules having a length of at least 20, 25, 30, 40, 50, 75 or 100 consecutive nucleotides in length, or between 50 and 400 nucleotides in length, are isolated from a blood, serum or plasma sample of a patient. The sequence of each of the circulating cell-free DNA molecules is determined, and compared with one or more of the sequences set forth in Tables A-D to determine whether the sequence of a circulating cell-free DNA falls within a chromosomal region set forth in Table 2, Table 3, or Table 4. If so, a diagnosis of prostate cancer is made. In the case of a patient treated with a therapy for prostate cancer, recurrence is indicated if a circulating cell-free DNA falls within a chromosomal region set forth in Table 2, Table 3, or Table 4 is detected. In preferred embodiments, a diagnosis of prostate cancer or prostate cancer treatment failure or recurrence is indicated if two or more circulating cell-free DNA molecules fall within 2, 3, 4 or more chromosomal regions set forth in Tables 2-4, preferably all such chromosomal regions being in the same table.

In another specific embodiment, substantially all circulating cell-free DNA molecules having a length of at least 20, 25, 30, 40, 50, 75 or 100 consecutive nucleotides in length, or between 50 and 400 nucleotides in length, are isolated from a blood, serum or plasma sample of a patient. These circulating cell-free DNA molecules are hybridized to a microarray that is described above in the context of the kit invention to determine if one of the circulating cell-free DNA molecules hybridizes to any one of a plurality of oligonucleotide probes under stringent conditions. Each of the oligonucleotide probes has a nucleotide sequence identical to a part of the sequence of a chromosomal region chosen from Tables 2-5 or a sequence set forth in Tables A-D). Thus, if a circulating DNA molecule hybridizes under stringent conditions to one of the oligonucleotide probes, it indicates that the circulating DNA molecule has a nucleotide sequence falling within a chromosomal region set forth in Table 2, Table 3, or Table 4. If so, a diagnosis of prostate cancer is made. In the case of a patient treated with a therapy for prostate cancer, recurrence is indicated if a circulating cell-free DNA falls within a chromosomal region set forth in Table 2, Table 3, or Table 4 is detected. In preferred embodiments, a diagnosis of prostate cancer or prostate cancer treatment failure or recurrence is indicated if two or more circulating cell-free DNA molecules fall within 2, 3, 4 or more chromosomal regions set forth in Tables 2-4, preferably all such chromosomal regions being in the same table, e.g., Table 2, Table 3, or Table 4.

In the above various embodiments, preferably the circulating cell-free DNA molecules have at least 25 consecutive nucleotides in length (preferably at least 50, 70, 80, 100, 120 or 200 consecutive nucleotides in length). More preferably, the circulating cell-free DNA molecules have between about 50 and about 300 or 400, preferably from about 75 and about 300 or 400, more preferably from about 100 to about 200 consecutive nucleotides of a unique sequence within a chromosomal region as set forth in Tables 2-5 (or of a unique sequence set forth in Tables A-D).

Detection of Circulating Nucleic Acids in the Blood

In order to detect the presence of circulating nucleic acids in the blood of patients that may have, or are suspected of having, prostate cancer, a blood sample is obtained from the patient. Serum or plasma from the blood sample is then analyzed for the presence of a circulating cell-free DNA or biomarker as described herein. Nucleic acids can be isolated from serum or plasma using well known techniques, see, e.g., the example sections. In the context of the current invention, the nucleic acid sequences that are analyzed are DNA sequences. Thus, in this section, methods described as evaluating "nucleic acids" refers to the evaluation of DNA.

Detection techniques for evaluating nucleic acids for the presence of a biomarker involve procedures well known in the field of molecular genetics. Further, many of the methods involve amplification of nucleic acids. Ample guidance for performing is provided in the art. Exemplary references include manuals such as PCR Technology: *Principles and Applications for DNA Amplification* (ed. H. A. Erlich, Freeman Press, NY, N.Y., 1992); *PCR Protocols: A Guide to Methods and Applications* (eds. Innis, et al., Academic Press, San Diego, Calif., 1990); Current Protocols in Molecular Biology, Ausubel, 1994-1999, including supplemental updates through April 2004; Sambrook & Russell, *Molecular Cloning, A Laboratory Manual* (3rd Ed, 2001).

Although the methods may employ PCR steps, other amplification protocols may also be used. Suitable amplification methods include ligase chain reaction (see, e.g., Wu & Wallace, *Genomics* 4:560-569, 1988); strand displacement assay (see, e.g., Walker et al., *Proc. Natl. Acad. Sci. USA* 89:392-396, 1992; U.S. Pat. No. 5,455,166); and several transcription-based amplification systems, including the methods described in U.S. Pat. Nos. 5,437,990; 5,409,818; and 5,399,491; the transcription amplification system (TAS) (Kwoh et al., *Proc. Natl. Acad. Sci. USA* 86:1173-1177, 1989); and self-sustained sequence replication (3SR) (Guatelli et al., *Proc. Natl. Acad. Sci. USA* 87:1874-1878, 1990; WO 92/08800). Alternatively, methods that amplify the probe to detectable levels can be used, such as Qβ-replicase amplification (Kramer & Lizardi, *Nature* 339:401-402, 1989; Lomeli et al., *Clin. Chem.* 35:1826-1831, 1989). A review of known amplification methods is provided, for example, by Abramson and Myers in *Current Opinion in Biotechnology* 4:41-47, 1993.

In some embodiments, the detection of biomarker in the CNA of a patient is performed using oligonucleotide primers and/or probes to detect a target sequence, wherein the target sequence is present in (e.g., comprises some unambiguously assigned portion of) any of the chromosomal regions listed in Table 2, Table 3, Table 4, or Table 5). Oligonucleotides can be prepared by any suitable method, usually chemical synthesis, and can also be purchased through commercial sources. Oligonucleotides can include modified phosphodiester linkages (e.g., phosphorothioate, methylphosphonates, phosphoamidate, or boranophosphate) or linkages other than a phosphorous acid derivative into an oligonucleotide may be used to prevent cleavage at a selected site. In addition, the use of 2'-amino modified sugars tends to favor displacement over digestion of the oligonucleotide when hybridized to a nucleic acid that is also the template for synthesis of a new nucleic acid strand.

In one embodiment, the biomarker is identified by hybridization under sequence-specific hybridization conditions with a probe that targets a chromosomal region described herein. The probe used for this analysis can be a long probe or sets for short oligonculeotide probes, e.g., from about 20 to about 150 nucleotides in length may be employed.

Suitable hybridization formats are well known in the art, including but not limited to, solution phase, solid phase, oligonucleotide array formats, mixed phase, or in situ hybridization assays. In solution (or liquid) phase hybridizations, both the target nucleic acid and the probe or primers are free to interact in the reaction mixture. Techniques such as real-time PCR systems have also been developed that permit analysis, e.g., quantification, of amplified products during a PCR reaction. In this type of reaction, hybridization with a specific oligonucleotide probe occurs during the amplification program to identify the presence of a target nucleic acid. Hybridization of oligonucleotide probes ensure the highest specificity due to thermodynamically controlled two state transition. Examples for this assay formats are fluorescence resonance energy transfer hybridization probes, molecular beacons, molecular scorpions, and exonuclease hybridization probes (e.g., reviewed in Bustin, *J. Mol. Endocrin.* 25:169-93, 2000).

Suitable assay formats include array-based formats, described in greater detail below in the "Device" section, where probe is typically immobilized. Alternatively, the target may be immobilized.

In a format where the target is immobilized, amplified target DNA is immobilized on a solid support and the target complex is incubated with the probe under suitable hybridization conditions, unhybridized probe is removed by washing under suitably stringent conditions, and the solid support is monitored for the presence of bound probe. In formats where the probes are immobilized on a solid support, the target DNA is typically labeled, usually during amplification. The immobilized probe is incubated with the amplified target DNA under suitable hybridization conditions, unhybridized target DNA is removed by washing under suitably stringent conditions, and the solid support/probe is monitored for the presence of bound target DNA.

In typical embodiments, multiple probes are immobilized on a solid support and the target chromosomal regions in the CNA from a patient are analyzed using the multiple probes simultaneously. Examples of nucleic acid arrays are described by WO 95/11995.

In an alternative probe-less method, amplified nucleic acid corresponding to a target nucleic acid present in a chromosomal region is performed using nucleic acid primers to the chromosomal region and is detected by monitoring the increase in the total amount of double-stranded DNA in the reaction mixture, is described, e.g., in U.S. Pat. No. 5,994,056; and European Patent Publication Nos. 487,218 and 512,334. The detection of double-stranded target DNA relies on the increased fluorescence various DNA-binding dyes, e.g., SYBR Green, exhibit when bound to double-stranded DNA.

As appreciated by one in the art, specific amplification methods can be performed in reaction that employ multiple primers to target the chromosomal regions such that the biomarker can be adequately covered.

DNA Sequencing

In preferred embodiments, the presence of a sequence from a chromosomal region set forth in Table 2, Table 3, Table 4 or Table 5 in the CNA from a patient undergoing evaluation is detected by direct sequencing. Such sequencing, especially using the Roche 454, Illumina, and Applied Biosystems sequencing systems mentioned below or similar advanced sequencing systems, can include quantitation (i.e., determining the level) of nucleic acids having a particular sequence. Such quantitation can be used in the embodiments of the invention that involve determining the level of a biomarker (some embodiments of which involve correlating a particular level to the presence or absence of cancer). Methods include e.g., dideoxy sequencing-based methods although other methods such as Maxam and Gilbert sequencing are also known (see, e.g., Sambrook and Russell, supra). In typical embodiments, CNA from a patient is sequenced using a large-scale sequencing method that provides the ability to obtain sequence information from many reads. Such sequencing platforms includes those commercialized by Roche 454 Life Sciences (GS systems), Illumina (e.g., HiSeq, MiSeq) and Applied Biosystems (e.g., SOLiD systems).

The Roche 454 Life Sciences sequencing platform involves using emulsion PCR and immobilizing DNA fragments onto bead. Incorporation of nucleotides during synthesis is detected by measuring light that is generated when a nucleotide is incorporated.

The Illumina technology involves the attachment of randomly fragmented genomic DNA to a planar, optically transparent surface. Attached DNA fragments are extended and bridge amplified to create an ultra-high density sequencing flow cell with clusters containing copies of the same template. These templates are sequenced using a sequencing-by-synthesis technology that employs reversible terminators with removable fluorescent dyes.

Methods that employ sequencing by hybridization may also be used. Such methods, e.g., used in the ABI SOLiD4+ technology uses a pool of all possible oligonucleotides of a fixed length, labeled according to the sequenced position. Oligonucleotides are annealed and ligated; the preferential ligation by DNA ligase for matching sequences results in a signal informative of the nucleotide at that position.

The sequence can be determined using any other DNA sequencing method including, e.g., methods that use semiconductor technology to detect nucleotides that are incorporated into an extended primer by measuring changes in current that occur when a nucleotide is incorporated (see, e.g., U.S. Patent Application Publication Nos. 20090127589 and 20100035252). Other techniques include direct label-free exonuclease sequencing in which nucleotides cleaved from the nucleic acid are detected by passing through a nanopore (Oxford Nanopore) (Clark et al., *Nature Nanotechnology* 4: 265-270, 2009); and Single Molecule Real Time (SMRT™) DNA sequencing technology (Pacific Biosciences), which is a sequencing-by synthesis technique.

Devices and Kits

In a further aspect, the invention provides diagnostic devices and kits useful for identifying one or more prostate cancer-associated biomarkers in the CNA from a patient where the one or more biomarkers is a sequence corresponding to any of the chromosomal regions set forth in Table 2, Table 3, Table 4, or Table 5. As will be apparent to skilled artisans, the kit of the present invention is useful in the above-discussed method for analyzing circulating cell-free DNA in a patient sample and in diagnosing, screening or monitoring prostate cancer as described above.

Thus, in one aspect, the present invention provides the use of at least one oligonucleotide for the manufacture of a diagnostic kit useful in diagnosing, screening or monitoring prostate cancer. The nucleotide sequence of the oligonucleotide falls within a chromosomal region set forth in Table 2, Table 3, Table 4, or Table 5 (or matches a part of a sequence set forth in Table A, Table B, Table C, or Table D).

Preferably, the kit of the present invention includes one, two or more (e.g., at least 1, 2, 3, 4, 5, 6, 7, 8, 9, 10, 12, 15, 20, 25, 30, 40 or at least 50, but preferably less than 111, preferably from one to about 50, more preferably from 2 to about 50, or from 3 to about 50 sets of oligonucleotides. Each set comprises one or more oligonucleotides (e.g., from about one to about 10,000, preferably from 50, 100, 200 or 300 to about 10,000). All of the nucleotide sequences of such one or more oligonucleotides in each set fall within the same one single chromosomal region that is set forth in Table 2, Table 3, Table 4, or Table 5 (or match a part of the same one single sequence set forth in Table A, Table B, Table C, or Table D). Each oligonucleotide should have from about 18 to 100 nucleotides, or from 20 to about 50 nucleotides, and is capable of hybridizing, under stringent hybridization conditions, to the chromosomal region in which its sequence falls. The oligonucleotides are useful as probes for detecting circulating cell-free DNA molecules derived from the chromosomal regions. Preferably, each set includes a sufficient number of oligonucleotides with sequences mapped to one chromosomal region such that any circulating cell-free DNA molecules derived from the chromosomal region can be detected with the oligonucleotide set. Thus, the number of oligonucleotides required in each set is determined by the total length of unique nucleotide sequence of a particular chromosomal region, as will be apparent to skilled artisans. Such total lengths are indicated in Tables 2-5 and should also be apparent from Tables A-D.

Preferably, in the kit of the present invention, different oligonucleotide sets correspond to different chromosomal regions within the same table. Preferably, the oligonucleotides are free of repetitive element. Optionally, the oligonucleotides are attached to one or more solid substrates such as microchips and beads. In preferred embodiments, the kit is a microarray with the above oligonucleotides.

In one embodiment, the kit of the present invention includes a plurality of oligonucleotide sets capable of hybridizing to the chromosomal regions set forth in Table 2, Table 3, Table 4, and Table 5, respectively. That is, the kit includes oligonucleotide probes corresponding to each and every chromosomal regions set forth in Tables 2, 3, 4, and 5 (or matching each and every sequence set forth in Tables A, B, C, and D) such that all circulating cell-free DNA derived from any chromosomal region set forth in Tables 2-5 can be detected using the kit.

Use of the oligonucleotides included in the kit described for the manufacture of the kit useful for diagnosing, screening or monitoring prostate cancer is also contemplated. The manufacturing of such kit should be apparent to a skilled artisan.

In some embodiments, a diagnostic device comprises probes to detect at least 2, 3, 4, 5, 6, 7, 8, 9, 10, 15, 20, 30, 40, 50, 60, 75, or 100, or all 110 chromosomal regions set forth in Tables 2-5. In some embodiments, the present invention provides probes attached to a solid support, such as an array slide or chip, e.g., as described in DNA Microarrays: A Molecular Cloning Manual, 2003, Eds. Bowtell and Sambrook, Cold Spring Harbor Laboratory Press. Construction of such devices are well known in the art, for example as described in US Patents and Patent Publications U.S. Pat. No. 5,837,832; PCT application W095/11995; U.S. Pat. Nos. 5,807,522; 7,157,229, 7,083,975, 6,444,175, 6,375,903, 6,315,958, 6,295,153, and 5,143,854, 2007/0037274, 2007/0140906, 2004/0126757, 2004/0110212, 2004/0110211, 2003/0143550, 2003/0003032, and 2002/0041420. Nucleic acid arrays are also reviewed in the following references: *Biotechnol Annu Rev* 8:85-101 (2002); Sosnowski et al, *Psychiatr Genet* 12(4):181-92 (December 2002); Heller, *Annu Rev Biomed Eng* 4: 129-53 (2002); Kolchinsky et al, *Hum. Mutat* 19(4):343-60 (April 2002); and McGail et al, Adv Biochem Eng Biotechnol 77:21-42 (2002).

Any number of probes may be implemented in an array. A probe set that hybridizes to different, preferably unique, segments of a chromosomal region may be used where the probe set detects any part of the chromosomal region. Alternatively, a single probe to a chromosomal region may be immobilized to a solid surface. Polynucleotide probe can be synthesized at designated areas (or synthesized separately and then affixed to designated areas) on a substrate, e.g., using a light-directed chemical process. Typical synthetic polynucleotides can be about 15-200 nucleotides in length.

The kit can include multiple biomarker detection reagents, or one or more biomarker detection reagents in combination with one or more other types of elements or components (e.g., other types of biochemical reagents, containers, packages such as packaging intended for commercial sale, substrates to which biomarker detection reagents are attached, electronic hardware components, etc.). Accordingly, the present invention further provides biomarker detection kits and systems, including but not limited to arrays/microarrays of nucleic acid molecules, and beads that contain one or more probes or other detection reagents for detecting one or more biomarkers of the present invention. The kits can optionally include various electronic hardware components; for example, arrays ("DNA chips") and microfluidic systems ("lab-on-a-chip" systems) provided by various manufacturers typically comprise hardware components. Other kits may not include electronic hardware components, but may be comprised of, for example, one or more biomarker detection reagents (along with, optionally, other biochemical reagents) packaged in one or more containers.

Biomarker detection kits/systems may contain, for example, one or more probes, or sets of probes, that hybridize to a nucleic acid molecule present in a chromosomal region set forth in Tables 2-5.

A biomarker detection kit of the present invention may include components that are used to prepare CNA from a blood sample from a patient for the subsequent amplification and/or detection of a biomarker.

Correlating the Presence of Biomarkers with Prostate Cancer

The present invention provides methods and reagents for detecting the presence of a biomarker in CNA from a patient that has prostate cancer or that is being evaluated to determine if the patient may have prostate cancer. In the context of the invention, "detection" or "identification" or "identifying the presence" or "detecting the presence" of a biomarker associated with prostate cancer in a CNA sample from a patient refers to determining any level of the biomarker in the CNA of the patient where the level is greater than a threshold value that distinguishes between prostate cancer and non-prostate cancer CNA samples for a given assay.

In the current invention, for example, the presence of any one of the chromosomal regions (i.e., biomarkers) listed in Tables 2-4 is indicative of prostate cancer. As appreciated by one of skill in the art, biomarkers may be employed in analyzing a patient sample where the biomarker has also been observed infrequently in a normal patient in order to increase the sensitivity of the detection. For example, the biomarkers indicated by bold font in Tables 2 and 3 have been observed to be present infrequently in CNA obtained from normal individuals; however, given the low frequency of occurrence in normal samples relative to the higher frequency of occurrence in prostate cancer, the presence of the biomarker in a patient indicates that the patient has a 95% or greater likelihood of having prostate cancer. Thus, for example, arrays used to detect the chromosomal regions can include those that identify the chromosomal regions in Tables 2 and 3 that are indicated in bold font.

The biomarkers set forth in Tables 2-4 are associated with prostate cancer, i.e., they are over-represented in prostate cancer patients compared to individuals not diagnosed with prostate cancer. Thus, the detection of one or more of the biomarkers set forth in Tables 2-4 is indicative of prostate cancer, i.e., the patient has an increased probability of having prostate cancer compared to a patient that does not have the biomarker. In some embodiments, the detection of two or more biomarkers set forth in Tables 2-4 in the CNA of a patient is indicative of a greater probability for prostate cancer. As understood in the art, other criteria, e.g., clinical criteria, etc., are also employed to diagnose prostate cancer in the patient. Accordingly, patients that have a biomarker associated with prostate cancer also undergo other diagnostic procedures.

In some embodiments, one or more biomarkers that are under-represented in prostate cancer may be detected in the CNA of a patient. Thus, for example, a biomarker listed in Table 5 may be detected in a CNA sample from a patient where the detection of the biomarker is indicative of a normal diagnosis, i.e., that the patient does not have prostate cancer.

"Over-represented" or "increased amount" means that the level of one or more circulating cell-free DNAs is higher than normal levels. Generally this means an increase in the level as compared to an index value. Conversely "under-represented" or "decreased amount" means that the level of one or more particular circulating cell-free DNA molecules is lower than normal levels. Generally this means a decrease in the level as compared to an index value.

In preferred embodiments, the test value representing the amount of a particular circulating cell-free DNA is compared to one or more reference values (or index values), and optionally correlated to prostate cancer or cancer recurrence. Optionally, an increased likelihood of prostate cancer is indicated if the test value is greater than the reference value.

Those skilled in the art are familiar with various ways of deriving and using index values. For example, the index value may represent the copy number or concentration of a particular cell-free DNA according to the present invention in a blood sample from a patient of interest in healthy state, in which case a copy number or concentration in a sample from the patient at a different time or state significantly higher (e.g., 1.5-fold, 2-fold, 3-fold, 4-fold, 5-fold, 10-fold, 20-fold, 30-fold, 40-fold, 50-fold, 100-fold or more higher) than this index value would indicate, e.g., prostate cancer or increased likelihood of cancer recurrence.

Alternatively, the index value may represent the average concentration or copy number of a particular circulating cell-free DNA for a set of individuals from a diverse cancer population or a subset of the population. For example, one may determine the average copy number or concentration of a circulating cell-free DNA in a random sampling of patients with prostate cancer. Thus, patients having a copy number or concentration (test value) comparable to or higher than, this value identified as having an increased likelihood of having prostate cancer or prostate cancer recurrence than those having a test value lower than this value.

Often the copy number or amount (e.g., concentration) will be considered "increased" only if it differs significantly from the index value, e.g., at least 1.5 fold difference in absolute or relative (e.g., as reflected by hybridization signal) copy number or concentration.

A useful index value may represent the copy number or concentration of a particular circulating cell-free DNA or of a combination (weighted or straight addition) of two or more circulating cell-free DNAs corresponding to the same chromosomal region or different chromosomal regions. When two or more biomarkers or circulating cell-free DNA molecules are used in the diagnosis/monitoring method, the presence or absence of, or the amount of, each biomarker or circulating cell-free DNA can be weighted and combined. Thus, a test value may be provided by (a) weighting the determined status or amount of each circulating cell-free DNA molecule with a predefined coefficient, and (b) combining the weighted status or amount to provide a test value. The combining step can be either by straight addition or averaging (i.e., weighted equally) or by a different predefined coefficient.

The information obtained from the biomarker analysis may be stored in a computer readable form. Such a computer system typically comprises major subsystems such as a central processor, a system memory (typically RAM), an input/output (I/O) controller, an external device such as a display screen via a display adapter, serial ports, a keyboard, a fixed disk drive via a storage interface and a floppy disk drive operative to receive a floppy disc, and a CD-ROM (or DVD-ROM) device operative to receive a CD-ROM. Many other devices can be connected, such as a network interface connected via a serial port.

The computer system may also be linked to a network, comprising a plurality of computing devices linked via a data link, such as an Ethernet cable (coax or 10 BaseT), telephone line, ISDN line, wireless network, optical fiber, or other suitable signal transmission medium, whereby at least one network device (e.g., computer, disk array, etc.) comprises a pattern of magnetic domains (e.g., magnetic disk) and/or charge domains (e.g., an array of DRAM cells) composing a bit pattern encoding data acquired from an assay of the invention.

The computer system can comprise code for interpreting the results of a study evaluating the presence of one or more of the biomarkers. Thus in an exemplary embodiment, the biomarker analysis results are provided to a computer where a central processor executes a computer program for determining the likelihood of a patient that has prostate cancer.

The invention also provides the use of a computer system, such as that described above, which comprises: (1) a computer; (2) a stored bit pattern encoding the biomarker testing results obtained by the methods of the invention, which may be stored in the computer; (3) and, optionally, (4) a program for determining the likelihood of a patient having prostate cancer.

The invention further provides methods of generating a report based on the detection of one or more biomarkers set forth in Tables 2-5.

Thus, the present invention provides systems related to the above methods of the invention. In one embodiment the invention provides a system for analyzing circulating cell-free DNA, comprising: (1) a sample analyzer for executing the method of analyzing circulating cell-free DNA in a patient's blood, serum or plasma as described in the various embodiments above (incorporated herein by reference); (2) a computer system for automatically receiving and analyzing data obtained in step (1) to provide a test value representing the status (presence or absence or amount, i.e., concentration or copy number) of one or more circulating cell-free DNA molecules having a nucleotide sequence of at least 25 nucleotides falling within a chromosomal region set forth in Table 2, Table 3, Table 4, or Table 5 (or having a nucleotide sequence that is a part of one of the sequences set forth in Table A, Table B, Table C, or Table D), and optionally for comparing the test value to one or more reference values each associated with a predetermined status of prostate cancer. In some embodiments, the system further comprises a display module displaying the comparison between the test value and the one or more reference values, or displaying a result of the comparing step.

Thus, as will be apparent to skilled artisans, the sample analyzer may be, e.g., a sequencing machine (e.g., Illumina HiSeq™, Ion Torrent PGM, ABI SOLiD™ sequencer, PacBio RS, Helicos Heliscope™, etc.), a PCR machine (e.g., ABI 7900, Fluidigm BioMark™, etc.), a microarray instrument, etc.

In one embodiment, the sample analyzer is a sequencing instrument, e.g., a next-generation sequencing instrument such as Roche's GS systems, Illumina's HiSeq and MiSeq, and Life Technologies' SOLiD systems. Circulating cell-free DNA molecules are isolated from a patient's blood or serum or plasma, and the sequences of all of the circulating cell-free DNA molecules are obtained using the sample analyzer. The sequencing instrument is used in sequencing the circulating cell-free DNA molecules, and obtaining the sequences of these molecules. A computer system is then employed for automatically analyzing the sequences to determine the presence or absence or amount of a circulating cell-free DNA molecule having a nucleotide sequence of at least 25 nucleotides falling within a chromosomal region set forth in Table 2, Table 3, Table 4, or Table 5 (or having a nucleotide sequence that is a part of one of the sequences set forth in Table A, Table B, Table C, or Table D) in the sample. For example, the computer system may compare the sequence of each circulating cell-free DNA molecule in the sample to each sequence in Tables A, B, C, and D to determine if there is a match, i.e., if the sequence of a circulating cell-free DNA molecule falls within a sequence in Table A, Table B, Table C, or Table 2 or within a chromosomal region set forth in Table 2, Table 3, Table 4, or Table 5. The copy number of a particular circulating cell-free DNA molecule is also automatically determined by the computer system. Optionally the computer system automatically correlates the sequence analysis result with a diagnosis regarding prostate cancer. For example, if one, two or more circulating cell-free DNA molecules are identified to be derived from a chromosomal region in Table 2, Table 3, or Table 4 and preferably two or more circulating cell-free DNA molecules with sequences falling within different chromosomal regions from one single table chosen from Tables 2-4, then the computer system automatically correlates this analysis result with a diagnosis of prostate cancer. Optionally, the computer system further comprises a display module displaying the results of sequence analysis and/or the result of the correlating step. The display module may be for example, a display screen, such as a computer monitor, TV monitor, or the touch screen, a printer, and audio speakers.

The computer-based analysis function can be implemented in any suitable language and/or browsers. For example, it may be implemented with C language and preferably using object-oriented high-level programming languages such as Visual Basic, SmallTalk, C++, and the like. The application can be written to suit environments such as the Microsoft Windows™ environment including Windows™ 98, Windows™ 2000, Windows™ NT, and the like. In addition, the application can also be written for the Macintosh™, SUN™, UNIX or LINUX environment. In addition, the functional steps can also be implemented using a universal or platform-independent programming language. Examples of such multi-platform programming languages include, but are not limited to, hypertext markup language (HTML), JAVA™, JavaScript™, Flash programming language, common gateway interface/structured query language (CGI/SQL), practical extraction report language (PERL), AppleScript™ and other system script languages, programming language/structured query language (PL/SQL), and the like. Java™- or JavaScript™-enabled browsers such as HotJava™, Microsoft™ Explorer™, or Netscape™ can be used. When active content web pages are used, they may include Java™ applets or ActiveX™ controls or other active content technologies.

The analysis function can also be embodied in computer program products and used in the systems described above or other computer- or internet-based systems. Accordingly, another aspect of the present invention relates to a computer program product comprising a computer-usable medium having computer-readable program codes or instructions embodied thereon for enabling a processor to carry out the analysis and correlating functions as described above. These computer program instructions may be loaded onto a computer or other programmable apparatus to produce a machine, such that the instructions which execute on the computer or other programmable apparatus create means for implementing the functions or steps described above. These computer program instructions may also be stored in a computer-readable memory or medium that can direct a computer or other programmable apparatus to function in a particular manner, such that the instructions stored in the computer-readable memory or medium produce an article of manufacture including instruction means which implement the analysis. The computer program instructions may also be loaded onto a computer or other programmable apparatus to cause a series of operational steps to be performed on the computer or other programmable apparatus to produce a computer implemented process such that the instructions which execute on the computer or other programmable apparatus provide steps for implementing the functions or steps described above.

The following examples are provided by way of illustration only and not by way of limitation. Those of skill in the art will readily recognize a variety of non-critical parameters that could be changed or modified to yield essentially similar results.

EXAMPLES

Example 1

Identification of Prostate Cancer-Associate CNA

Sequencing of CNA:

Sera from 197 patients having biopsy-proven prostate cancer with a Gleasson Score of 3 to 10 were used. The data were compared to samples obtained from 92 male apparently healthy blood donors (normals).

After extraction of DNA from serum or plasma, using standard silica based methods, a whole genome amplification was performed in duplicate. The products were pooled and used for further analysis.

Long Sequencing Runs:

The primer sequences for 454 sequencing were added to the product using fusion primers in not more than 20 cycles of PCR. The resulting product was treated according to the 454 sequencer manual and used for direct sequence detection.

Computational Analysis:

The sequence reads were appointed to the sample source by reading the identifier sequence string and all non source parts were cut out (e.g. primers).

The origin of the circulating DNA was investigated by local alignment analyses using the BLAST program using high stringent parameters (30). Repetitive elements were detected and masked by using a local install of the Repeatmasker software package (31) using the repbase (version 12.09) that was obtained from the Genetic Information Research Institute (32). After masking of the repetitive elements and region of low sequence complexity each sequence was subjected to sequential BLAST analyses querying databases of bacterial, viral and fungal genomes and the human genome (reference genome build 37.1). Bacterial, viral, fungal and human genomes were obtained from the National Center for Biotechnology Information (NCBI, (ftp.ncbi.nih.gov)). After each of the sequential database searches all parts of a queried sequence that produced significant hits (e<0.0001) were masked and masked sequences were subsequently used to query the next database. Masked nucleotides were counted and subtracted from the total nucleotide counts resulting in the amounts of unidentified nucleotides.

For each query fragment and each database search, the highest scoring BLAST hit with a length of more than 50% of the query sequence was recorded in a SQL database. The highest scoring BLAST hit was defined as the longest hit with the highest percent identity (maximum of hitlength× identity). For each of the sequences, the start and stop positions for query and database were recorded.

Disease Association Analysis:

To investigate which sequences/sequence tags are disease associated, all alignments that could be unambiguously placed on the human genomic database (*Homo sapiens* Build 37.1 ncbi nlm mapview website) were used. Those were categorized into 4060 region of 750,000 bp intervals and selected for differences between normal controls and cancer patients on the basis of a group comparison using the non-parametric median test. Five hundred chromosomal regions having the lowest p-values were used for further analyses.

In 347 rounds of bootstrap random selected samples linear multivariate regressions modeling was performed using the above selected 750k regions as independent parameters. The 347 rounds of bootstrap yielded $8.9 \times 10^7$ models. From these, the best 42 independent variables (750k pieces, based on $\Sigma AIC\omega_i$) were chosen and are shown in Table 1.

Selection of Clusters in the Pre-Selected Regions

As a second step, a cluster search within the 42 regions was performed and clusters of cancer samples were found that did not contain any normal samples. Additional clusters were searched where only one or fewer normal samples were found in a cluster of at least 10 cancer samples. The cluster regions were restricted to those that had a distance to the next normal hit of at least 200bp. Given these limits, 88 clusters were found, of which 25 contained one hit in the normal group. A sample is called positive if at least one hit is found in any of the cluster regions (see Table 2). A selection of 30 clusters without false positives covering 441 kbp was sufficient to provide a 94% sensitivity and 100% specificity, which can be increased to 96% when two more clusters with a hit in one normal was included, achieving a specificity of 99%.

Selection of Genomic Clusters

A search for genomic clusters was also performed over the whole non-repetitive genome. The limit was set to have more than 18 independent patients hits per cluster, where over 600 clusters with not more than 1 hit in samples from normals was found. A selection of 22 clusters covering about 475 kbp was sufficient to give a rate of 99.5% true positives at a 99% true negative level (see Table 3). Excluding those two regions that had one hit in the group of normal, non-prostate cancer patients, the true positive rate was 96% and consequently 100% specificity.

Example 2

Identification of Additional Biomarkers that are Over- or Under-Represented in Prostate Cancer In a further analysis to identify biomarkers, a subset of 77 Prostate Cancer samples and 70 Controls were sequenced on a Life Technologies SOLiD4+ System, which is a high-throughput sequencer that typically can run hundreds of millions of sequences of lengths of about 30 to about 75 bases in parallel. (Another example of such a sequencing technology is the Genome Analyzer (Illumina)). Briefly, samples were prepared as described for the 454 sequencing, where adaptors specific to SOLiD sequencing are used. For each sample about 5 million reads of 40 bp were achieved and aligned to the human genome (Build Hg18) using the Lifetechnologies "Bioscope" software suite with default stringency values. All uniquely aligned reads were used for further analysis.

In order to define the chromosomal regions, where samples of either group cluster in comparison the second group, all hits are ranked in order of their appearance on the chromosomes. Biomarker regions were initially defined as those regions where at least 15 hits covering at least 10 samples of a group were counted, but not more than one sample of the other group demonstrated a hit.

In 1000 round of random resampling the samples were divided into a training and validation set of 50% of each group. For each region, a sample in the region was assigned a score of 1 if the cluster was a prostate cancer (PrCa) cluster and a score of −1 for region where normal samples clustered. The average AUC for the validation set was found to be 0.92 if the score sums of 42 cluster regions are used. The regions used in the 1000 round of re-sampling were ranked according to the number of round in which either region participated. Tables 4 and 5 shows the 56 highest ranking regions. Table 4 summarizes those clusters identified in this analysis that were overrepresented in prostate cancer serum samples. Table 5 summarizes clusters identified in this analysis that were underrepresented in prostate cancer serum samples; the ROC curve using the 42 highest ranking regions is shown in FIG. 1. The AUC below the ROC curve was calculated as 0.96 (0.886-0.996) with and accuracy of 92% (86%-97%).

All patents, patent applications, and other published reference materials cited in this specification are hereby incorporated herein by reference in their entirety for their disclosures of the subject matter in whose connection they are cited herein.

---

Lengthy table referenced here

US11414706-20220816-T00001

Please refer to the end of the specification for access instructions.

---

Lengthy table referenced here

US11414706-20220816-T00002

Please refer to the end of the specification for access instructions.

---

Lengthy table referenced here

US11414706-20220816-T00003

Please refer to the end of the specification for access instructions.

---

Lengthy table referenced here

US11414706-20220816-T00004

Please refer to the end of the specification for access instructions.

Lengthy table referenced here

US11414706-20220816-T00005

Please refer to the end of the specification for access instructions.

Lengthy table referenced here

US11414706-20220816-T00006

Please refer to the end of the specification for access instructions.

Lengthy table referenced here

US11414706-20220816-T00007

Please refer to the end of the specification for access instructions.

Lengthy table referenced here

US11414706-20220816-T00008

Please refer to the end of the specification for access instructions.

Lengthy table referenced here

US11414706-20220816-T00009

Please refer to the end of the specification for access instructions.

LENGTHY TABLES

The patent contains a lengthy table section. A copy of the table is available in electronic form from the USPTO web site (https://seqdata.uspto.gov/?pageRequest=docDetail&DocID=US11414706B2). An electronic copy of the table will also be available from the USPTO upon request and payment of the fee set forth in 37 CFR 1.19(b)(3).

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11414706B2). An electronic copy of the "Sequence Listing" will also be available from the USPTO upon request and payment of the fee set forth in 37 CFR 1.19(b)(3).

What is claimed is:

1. A method of analyzing a sample from a patient for cell-free DNA associated with prostate cancer to calculate a numeric index of tumor-associated copy number variability, the method comprising:
   (a) isolating cell-free DNA from a blood, serum, or plasma sample from the patient;
   (b) sequencing cell-free DNA molecules and:
      (i) for a plurality of circulating cell-free DNA molecules, assigning each cell-free DNA sequences to one or more genomic regions, and selecting those cell-free DNA sequences that are unique sequences for their respective genomic region; and
      (ii) determining a normalized copy number of each selected cell-free DNA molecule;
   (c) comparing the normalized copy number of each selected cell-free DNA molecule to a reference distribution obtained from known cancer free individuals;
   (d) summing all normalized copy number values of regions having a normalized copy number value exceeding the 95% percentile of the reference distribution;
   (e) summing all negative normalized copy number values of regions that have a normalized copy number value less than the 5% percentile of the reference distribution; and
   (f) obtaining the numeric index of tumor-associated copy number variability using the sums obtained in (d) and (e), thereby analyzing the sample from the patient for cell-free DNA associated with prostate cancer.

2. The method of claim 1, wherein the numeric index value of (f) is compared to the distribution of the numeric index value obtained from cancer-free control subjects, where a numeric index value exceeding the $95^{th}$ percentile of the distribution of the numeric index value of the control population is indicative of cancer.

3. the method of claim 1, wherein cell-free DNA sequences selected in (b) comprises one or more sequences from Table 2, Table 3, Table 4, or Table 5.

* * * * *